US00PP07763P

United States Patent [19]

VandenBerg

[11] Patent Number: Plant 7,763

[45] Date of Patent: Jan. 7, 1992

[54] CHRYSANTHEMUM PLANT NAMED DENVER

[75] Inventor: Cornelis P. VandenBerg, Salinas, Calif.

[73] Assignee: Yoder Brothers, Inc., Barberton, Ohio

[21] Appl. No.: 570,619

[22] Filed: Aug. 21, 1990

[51] Int. Cl.[5] ..... A01H 5/00

[52] U.S. Cl. ..... Plt./74

[58] Field of Search ..... Plt./74, 82.1

*Primary Examiner*—Howard J. Locker

*Attorney, Agent, or Firm*—Foley & Lardner

[57] ABSTRACT

A Chrysanthemum plant named Denver particularly characterized by its flat capitulum form; daisy capitulum type; clear white ray floret color; diameter across face of capitulum of 57 to 70 mm when fully opened when grown as a pinched spray pot mum; photoperiodic response to short days of 48 to 53 days; plant height of 20 to 28 cm when grown as a pinched pot mum; and spreading branching pattern, with 4 to 5 breaks per plant after pinch.

3 Drawing Sheets

The present invention comprises a new and distinct cultivar of Chrysanthemum, botanically known as *Dendranthema grandiflora,* and referred to by the cultivar name Denver.

Denver, identified as 84-431012, was originated from a cross made by Cornelis P. VandenBerg in a controlled breeding program in Salinas, Calif. in 1984.

The female parent of Denver was an unnamed seedling, identified as 85-00501, and described as a white flat daisy pot spray mum having a flowering response to short days of 50 to 56 days under normal conditions, a height of 25 to 33 cm with 14 to 21 long days after the sticking of unrooted cuttings and 1 to 2 applications of 2500 ppm B-9 SP, semispreading breaking action with 3 to 6 breaks after pinch, and a diameter of capitulum of 64 to 76 mm. The female parent was discarded from the breeding program in October 1986.

The male parent of Denver was an unnamed seedling, identified as 82-040003, and described as a white flat spooned anemone spray pot mum having flowering response to short days of 50 to 61 days under normal conditions, a plant height of 23 to 28 cm with 15 to 19 long days sticking unrooted cuttings and 0 to 1 applications of 2500 ppm B-9 SP, spreading breaking action with 4 to 6 breaks per plant after pinch, and a diameter of capitulum of 51 to 64 mm. The male parent was discarded from the breeding program in May 1988.

Denver was discovered and selected as one flowering plant within the progeny of the stated cross by Cornelis P. Vandenberg in April 1985, in a controlled environment in Salinas, Calif.

The first act of asexual reproduction of Denver was accomplished when vegetative cuttings were taken from the initial selection in June 1985 in a controlled environment in Salinas, Calif. by technicians working under the supervision of Cornelis P. VandenBerg.

Horticultural examination of controlled flowerings of successive plantings has shown that the unique combination of characteristics as herein disclosed for Denver are firmly fixed and are retained through successive generations of asexual reproduction.

Denver has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice.

The following traits have been repeatedly observed and are determined to be basic characteristics of Denver, which, in combination, distinguish this Chrysanthemum as a new and distinct cultivar:

1. Flat capitulum form.
2. Daisy capitulum type.
3. Clear white ray floret color.
4. Diameter across face of capitulum of 57 to 70 mm. when fully opened, when grown as a pinched spray pot mum.
5. Photoperiodic flowering response to short days of 48 to 53 days.
6. Plant height, with 15 to 18 long days after sticking unrooted cuttings and with 1 to 2 applications of 2500 ppm B-9 SP, ranging from 20 to 28 cm when grown as a pinched pot mum with 4 cuttings in a 15 cm pot.
7. Branching pattern is spreading, each plant having 4 to 5 laterals after pinch.

The accompanying photographic drawings show typical inflorescence and leaf characteristics of Denver, with the colors being as nearly true as possible with illustrations of this type.

Sheet 1 is a color photograph of Denver grown as a pinched spray pot mum with 4 cuttings in a 15 cm. pot.

Sheet 2 is a black and white photograph of three views of the inflorescence of Denver.

Sheet 3 is a black and white photograph showing the upper and under sides of the leaves of Denver at 3 stages of development (mature, intermediate and immature).

Sheets 2 and 3 include a measuring tape in centimeters, thereby illustrating the dimensions of the flower and leaves.

Of the commerical cultivars known to the inventor, the most similar in comparison to Denver is the cultivar Solo, disclosed in U.S. Plant Pat. No. 6,058. Reference is made to attached Chart A, which compares certain characteristics of Denver to the same characteristics of Solo.

Similar traits are capitulum form and type, flowering response to short days, plant height and branching pattern, although Solo sometimes has one more break per plant after pinch than Denver. Denver has a large diameter of capitulum and a clear white ray floret color, compared to the off-white ray floret color (155B) of Solo. In addition, Denver has no pollen, while Solo has abundant pollen. The presence of pollen in a commercial variety often is regarded as a negative trait of that cultivar, because of the possibility of staining of furniture and clothing. Also, Denver has a more formal flower form than Solo, with Denver having more pointed ray florets compared to the rounded ray florets of Solo. When compared with both parents, Denver has a faster flowering response than both parents. The flower size of Denver is smaller than that of the female parent, and is larger than that of the male parent. Capitulum type of Denver is similar to that of the female parent, but significantly different from the spooned anemone type of the male parent.

In the following description color references are made to The Royal Horticultural Society Colour Chart. The color values were determined on plant material grown as a pinched spray pot mum in Salinas, Calif. on May 4, 1990. The clear white ray floret color of Denver is not represented in the R.H.S. Colour Chart.

Classification:

*Botanical.*—Dendranthema grandiflora cv Denver.

*Commercial.*—Daisy spray pot mum.

INFLORESCENCE

A. Capitulum:

*Form.*—Flat.

*Type.*—Daisy.

*Diameter across face.*—57 to 70 mm. When fully opened.

Corolla of ray florets:

*Color (general tonality from a distance of three meters).*—Clear white.

*Color.*—Upper surface: Clear white. Under surface: Clear white.

*Shape.*—Straight, pointed, slightly ribbed.

C. Corolla of disc florets:

*Color (mature).*—12B.

*Color (immature).*—12B, overlaid with 144B.

D. Reproductive organs:

*Androecium.*—Present on disc florets only; no pollen.

*Gynoecium.*—Present on both ray and disc florets.

PLANT

A. General Appearance:

*Height.*—20 to 28 cm when grown as a pinched pot mum in a 15 cm pot with 15 to 18 long days after direct sticking of unrooted cuttings and 1 to 2 applications of 2500 ppm B-9 SP.

*Branching pattern.*—Spreading, with 4 to 5 laterals after pinch.

B. Foliage:

*Color (upper surface).*—147A.

*Color (under surface).*—147B.

*Shape.*—See photograph.

CHART A

| CULTIVAR | DENVER | SOLO |
|---|---|---|
| Ray floret color | Clear white | White |
| Capitulum form and type | Flat daisy | Flat daisy |
| Diameter across face of capitulum | 57 to 70 mm | 50 to 60 mm |
| Flowering response | 48 to 53 days | 46 to 55 days |
| Plant height with 15 to 18 long days | 20 to 28 cm | 18 to 33 cm |
| Branching pattern | Spreading 4 to 5 laterals | Spreading 4 to 6 laterals |

COMPARISONS MADE OF PLANTS GROWN AS PINCHED SPRAY POT MUMS IN SALINAS, CALIFORNIA

I claim:

1. A new and distinct Chrysanthemum plant named Denver, as described and illustrated.

* * * * *

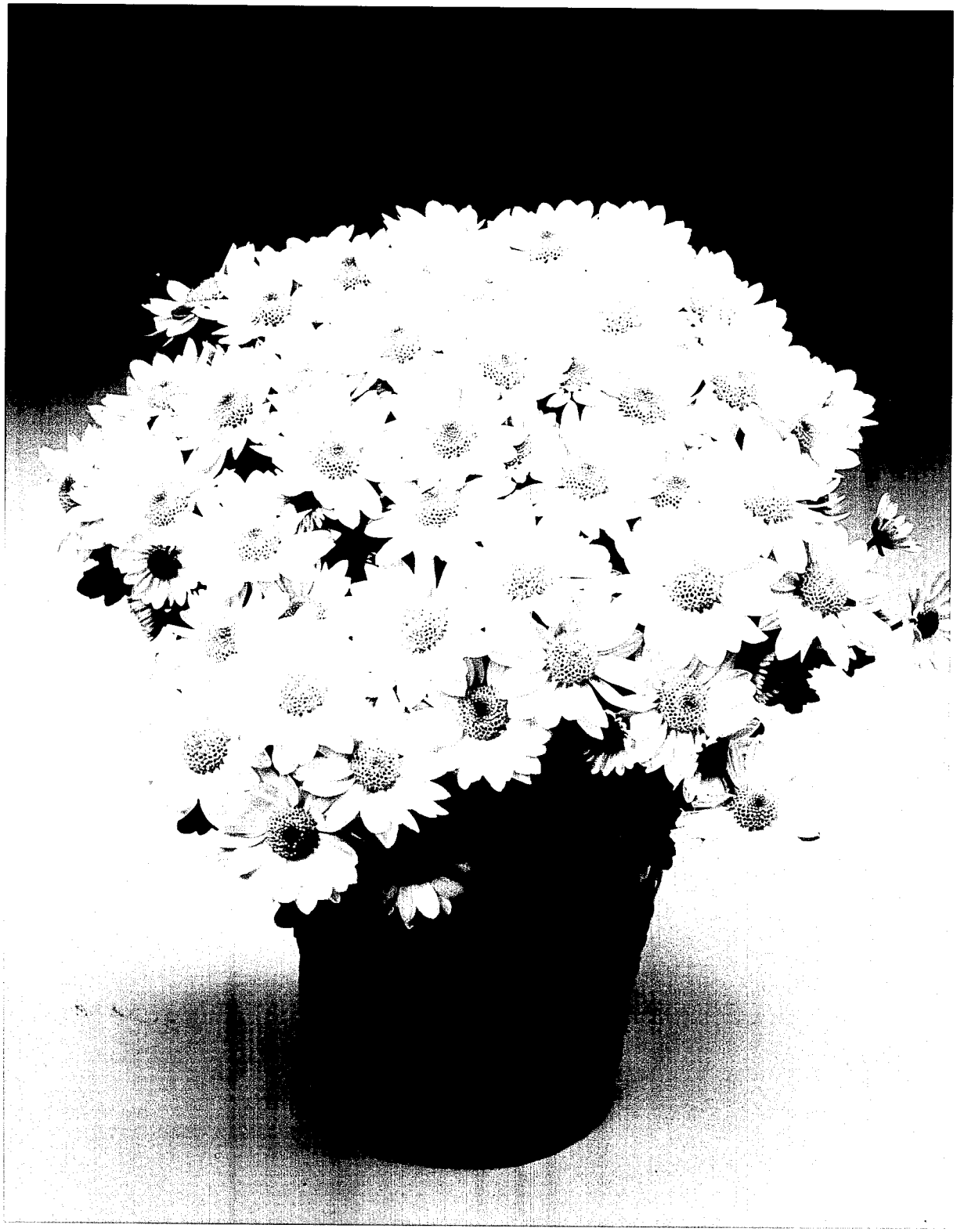

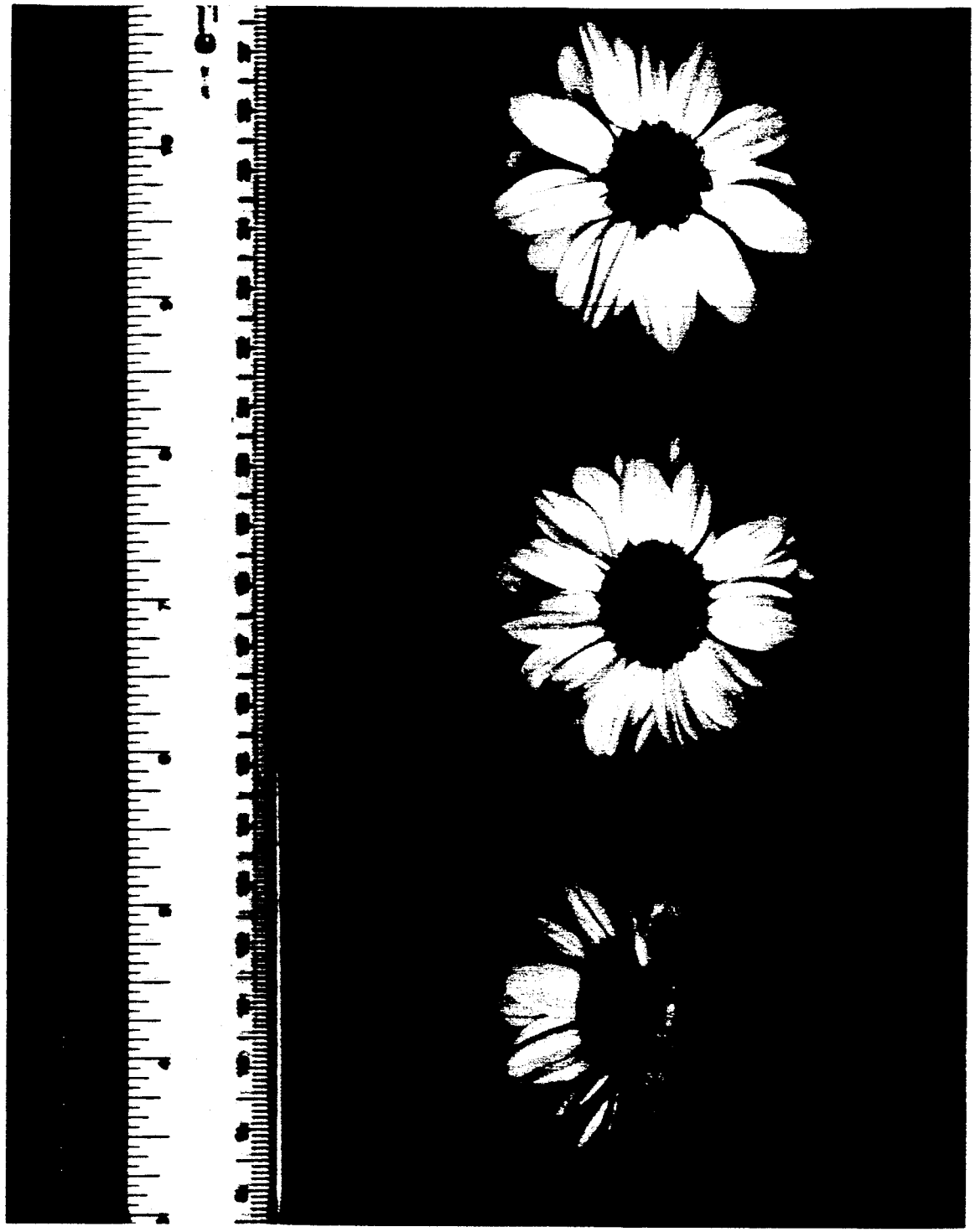

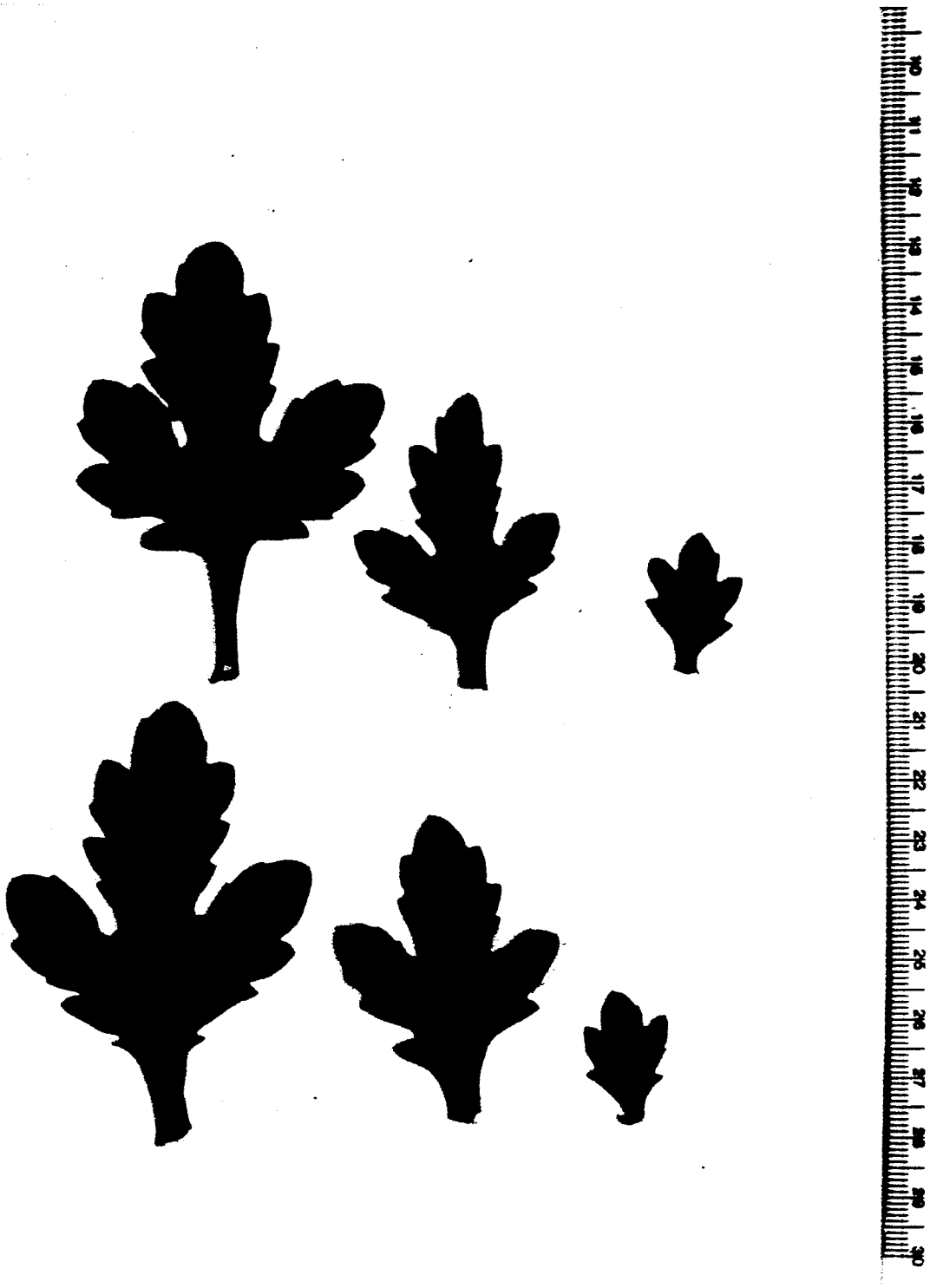

UNITED STATES PATENT AND TRADEMARK OFFICE

CERTIFICATE OF CORRECTION

PATENT NO. : PP 7,763

DATED : January 7, 1992

INVENTOR(S) : Cornelis P. VANDENBERG

It is certified that error appears in the above-identified patent and that said Letters Patent is hereby corrected as shown below:

Column 1, line 9, "85-00501" should read --80-005001--.

Column 1, line 23, "days sticking" should read --days after sticking--.

Column 1, line 30, "Vandenberg" should read --VandenBerg--.

Column 3, line 2, "large" should read --larger--.

Column 3, line 37, "mm. When" should read --mm. when--.

Sheet 2 of 3 of Drawings, "Jan. 7, 1991" (the date of patent) should read --Jan. 7, 1992--.

Sheet 3 of 3 of Drawings, "Jan. 7, 1991" (the date of patent) should read --Jan. 7, 1992--.

Signed and Sealed this

Second Day of November, 1993

*Attest:*

*Attesting Officer*

BRUCE LEHMAN

*Commissioner of Patents and Trademarks*